United States Patent [19]

Meyer

[11] Patent Number: 5,233,094
[45] Date of Patent: Aug. 3, 1993

[54] PROCESS FOR THE PREPARATION OF PERFLUORINATED ETHERS

[75] Inventor: Matthias Meyer, Hamburg, Fed. Rep. of Germany

[73] Assignee: Hoechst Aktiengesellschaft, Frankfurt am Main, Fed. Rep. of Germany

[21] Appl. No.: 975,084

[22] Filed: Nov. 12, 1992

[30] Foreign Application Priority Data

Nov. 16, 1991 [DE] Fed. Rep. of Germany ....... 4137783

[51] Int. Cl.$^5$ .............................................. C07C 41/22
[52] U.S. Cl. ...................................... 568/615; 568/683
[58] Field of Search ................................. 568/615, 683

[56] References Cited

U.S. PATENT DOCUMENTS 3,595,925  7/1971  Garth .................................. 260/615

FOREIGN PATENT DOCUMENTS 0154297  9/1985  European Pat. Off. .

Primary Examiner—Howard T. Mars
Attorney, Agent, or Firm—Connolly & Hutz

[57] ABSTRACT

The invention relates to a process for the preparation of perfluorinated ethers of the formula (I)

$$R-CF_2-CF_3 \qquad (I)$$

in which R is the radical $CF_3(CF_2)_2-O-[CF(CF_3)CF_2-O]_n-$, in which n is an integer from 0 to 60, from compounds of the formula (II)

$$R-[CF(CF_3)CF_2-O-]CHF-CF_3 \qquad (II)$$

by heating these at 150°–350° C. in the presence of at least one of the compounds $AlCl_3$, $AlBr_3$ or $AlF_3$.

5 Claims, No Drawings

PROCESS FOR THE PREPARATION OF PERFLUORINATED ETHERS

DESCRIPTION

The invention relates to a process for the preparation of perfluorinated ethers of the formula (I)

$$R-CF_2-CF_3 \quad (I)$$

in which R is the radical $CF_3(CF_2)_2-O-[CF(CF_3)CF_2-O]_n-$, in which n is an integer from 0 to 60, from compounds of the formula (II)

$$R-[CF(CF_3)CF_2-O-]CHF-CF_3 \quad (II).$$

Perfluoroethers of the formula (I) are distinguished by a high heat stability, and they are non-combustible and chemically stable, even against attacks by powerful oxidizing agents. The square brackets used in formula (II) are only for better understanding, and in principle can also be omitted, to give the equivalent formula $R-CF(CF_3)CF_2-O-CHF-CF_3$.

Because of their particular physical properties, in particular favorable viscosity properties within wide temperature ranges, high boiling points coupled with simultaneously low pour points, low surface tension and extreme dielectric properties, perfluorinated polyethers find diverse uses as inert liquids, dielectrics, heat exchange media, hydraulic oils and lubricants in the presence of highly aggressive media.

The oligomerization of hexafluoropropene oxide (HFPO) in the presence of CsF and polyethylene glycol dimethyl ethers, in particular tetraethylene glycol dimethyl ether, is described in EP-A-0 154 297. The crude oligomer is in general obtained here as a mixture having a molecular weight distribution of about 300-20000 g/mol. It consists of perfluoroether-acyl fluorides of the formula $R-[CF(CF_3)CF_2-O-]CF(CF_3)-COF$, in which R has the abovementioned meaning.

The acyl fluorides mentioned are sensitive to hydrolysis, split off aggressive and toxic fluorinated fragments at high temperatures, and therefore cannot be employed as inert liquids.

The reaction of these perfluoroether-acyl fluorides with AlCl₃ and/or AlBr₃ to give perfluorinated ethers of the formula (I) is described in German Patent Application P 4120508.1.

In contrast, according to EP-A-0 154 297, the acyl fluorides are hydrolyzed to carboxylic acids, these are converted into the salts and these salts are then decarboxylated in the presence of alkaline media. However, only incompletely fluorinated ethers of the formula $R-[CF(CF_3)CF_2-O-]CHF-CF_3$, which, although they are not sensitive to hydrolysis, are unstable at higher temperatures in the presence of atmospheric oxygen, are obtained by this route. U.S. Pat. No. 3,595,925 describes the reaction of these compounds using equimolar amounts of SbF₅ to give the perfluorinated compounds of the formula (I) in accordance with the equation:

$$R-[CF(CF_3)CF_2-O-]CHF-CF_3 + SbF_5 \rightarrow R-[CF(CF_3)CF_2-O-]CF_2-CF_3 + HF + SbF_3.$$

A disadvantage of this process is the use of expensive antimony pentafluoride.

Surprisingly, it has been found that the incompletely fluorinated ethers mentioned can be converted in the presence of aluminum halides into perfluorinated ethers having a chain shortened by 3 carbon atoms.

The invention relates to a process for the preparation of perfluorinated ethers of the formula (I)

$$R-CF_2-CF_3 \quad (I)$$

in which R is the radical $CF_3(CF_2)_2-O-[CF-(CF_3)CF_2-O-]_n-$, in which n is an integer from 0-60, from compounds of the formula (II)

$$R-[CF(CF_3)CF_2-O-]CHF-CF_3 \quad (II)$$

which comprises heating the compounds of the formula (II) at 150°-350° C. in the presence of at least one of the compounds AlCl₃, AlBr₃ or AlF₃.

The starting compounds of the formula (II), for example, are heated to the reaction temperature with at least one of the compounds AlCl₃, AlF₃ or AlBr₃ in a stirred flask under an inert gas atmosphere. Preferably, however, the compounds (II) are initially introduced into the flask and are heated, and the aluminum halide is then added. No solvent is necessary.

The amounts of aluminum halide added are in general 1 to 100 mol %, based on the amount of compound (II) employed, preferably 5-10 mol %.

The reaction temperature is 150°-300° C., preferably 200°-280° C., in particular 240°-260° C.

The fluorinated compounds of the general formula (II)

$$R-[CF(CF_3)CF_2-O-]CHF-CF_3 \quad (II)$$

in which R is the radical $CF_3(CF_2)_2-O-[CF(CF_3)CF_2-O-]_n-$ and n is an integer from 0-60, are employed. The value of n can be controlled by the temperature during the oligomerization of HFPO in accordance with EP-A-0 154 297. The lower the temperature chosen, the higher the value of n. Values of n=10 to n=60 are of particular interest. A mixture of acyl fluorides of the formula $R-[CF(CF_3)CF_2-O-]CF(CF_3)-COF$ is formed in the oligomerization of HFPO. The compounds of the formula (II) are obtained in accordance with EP-A-0 154 297 by hydrolysis and decarboxylation of these acyl fluorides with aqueous potassium hydroxide solution in ethylene glycol at 175° C. The compounds of the formula (II) are purified by extraction to remove ethylene glycol, filtration to remove potassium fluoride and subsequent drying, before they are employed in the process according to the invention.

The reaction of the compounds (II) can be monitored by IR and ¹⁹F-NMR spectroscopy, and has ended when the CH band at about 3000 cm⁻¹ in the IR spectrum has disappeared and the signals of the —CHFCF₃ end group are no longer visible in the ¹⁹F-NMR spectrum.

When the reaction has ended, the solid aluminum halide is removed by filtration.

The colorless filtrate can be passed for fractionation into boiling ranges by flash distillation without further purification steps.

EXAMPLES

Test Report

Preparation of the Starting Material (II) According to EP-A-0 154 297

A solution of 20 g of CsF in 50 ml of tetraethylene glycol dimethyl ether (tetraglyme) and 56 g of hexafluoropropylene oxide were initially introduced into a 4 l V-4A autoclave under a nitrogen atmosphere. 250 ml of $^R$Frigen F113 ($CCl_2FCClF_2$) were additionally added for dilution. 4000 g of hexafluoropropylene oxide were then passed in at a temperature of $-5°$ C. over a period of 8 hours, while mixing thoroughly. When the reaction had ended, the mixture was warmed to room temperature and the crude acyl fluoride oligomer formed was discharged under an $N_2$ atmosphere.

3000 g of this acyl fluoride oligomer $R—[CF(CF_3)CF_2—O—]CF(CF_3)—COF$ having an average molecular weight of 3000 g mol$^{-1}$ were initially introduced into a 4 l three-necked flask. 60 g of KOH were dissolved in a solution of 500 ml of diethylene glycol and 200 ml of water, and the solution was slowly added to the acyl fluoride oligomer. The reaction solution was first stirred at a temperature of 90° C. for 3 hours, and was then heated at 175° C. for about 6 hours. When the reaction had ended, the lower organofluorine phase, which contained the compound $R—[CF(CF_3)CF_2—O—]CHF—CF_3$ was separated from the glycol/water phase. The organofluorine phase was diluted with 1000 ml of Frigen F113, and then washed with water, subsequently with dilute HCl and with water again. After the residual content of water, Frigen F113 and diethylene glycol had been removed, the compounds (II) $R—[CF(CF_3)CF_2—O—]CHF—CF_3$ were obtained under reduced pressure at 200° C.

EXAMPLE 1

3 g of $AlCl_3$ (=22 mmol) were added to 300 g (0.23 mol) of a mixture of compounds of the formula (II) having an average molecular weight of 1300 g mol$^{-1}$ (obtained by flash distillation of the starting material prepared in accordance with the test report), and the mixture was heated at 250° C. under an $N_2$ atmosphere. The reaction was monitored by $^{19}$F-NMR spectroscopy, and had ended after 7 hours. The product was separated off from the solid $AlCl_3$ by filtration. 245 g of a water-clear filtrate were obtained (yield: 92 %).

The product was characterized with the aid of IR and $^{19}$F-NMR spectroscopy. Elemental analysis gave the values to be expected from formula (I) for the elements C, F and O.

EXAMPLE 2

300 g of a mixture of compounds of the formula (II) obtained as in Example 1 were heated to 225° C. under an inert gas atmosphere, and 2 g of $AlCl_3$ were added in portions. The reaction had ended after 4 hours. After working up as in Example 1, 255 g of an oligomer of the formula (I) were obtained (yield: 96 %). The product was characterized as described in Example 1.

EXAMPLE 3

1.3 g of $AlCl_3$ were added to 300 g (0.1 mol) of a mixture of compounds of the formula (II) having an average molecular weight of 3000 g mol$^{-1}$, and the mixture was heated at 270° C. The reaction had ended after 2 hours. Working up of the product was carried out as in Examples 1 and 2. 268 g of perfluorinated compounds (I) were obtained (yield: 94 %). The product was characterized as in Example 1.

EXAMPLE 4

The procedure was analogous to Example 3. However, instead of $AlCl_3$, 0.9 g of $AlF_3$ was added. The reacted had ended after 3 hours.

After working up, as described in Example 3, 265 g of perfluorinated product (I) were obtained (yield: 90 %). The product was characterized as in Example 1.

EXAMPLE 5

The procedure was analogous to Example 3, but instead of $AlCl_3$, 2.7 g of $AlBr_3$ were employed. 236 g of perfluorinated compounds (I) were obtained (yield: 83 %). The product was characterized as in Example 1.

EXAMPLE 6

1.2 g of $AlCl_3$ were added to 100 g (0.09 mol) of a perfluorinated compound of the formula (II) where n is 5 (obtained by disstillation of an acyl fluoride mixture prepared at $+5°$ C. and subsequent hydrolysis and decarboxylation of the individual acyl fluoride obtained by this procedure, of the formula $CF_3(CF_2)_2—O—[CF(CF_3)CF_2—O]_nCF(CF_3)COF$ where n is 5), and the mixture was heated at a temperature of 240° C. After a reaction time of two hours, 75 g of a readily mobile liquid which, according to analysis by $^{19}$F-NMR and gas chromatography, had the formula (I), where n is 4, were distilled off from the reaction mixture via a column at 222° C. (yield: 86%). The product was characterized as in Example 1.

EXAMPLE 7

13,500 g (3.65 mol) of a mixture of compounds of the formula (II) having an average molecular weight of 3700 g mol$^{-1}$ were heated to 250° C., and 48 g of $AlCl_3$ were added, distributed over a period of 16 hours. The mixture was stirred for a further 2 hours and the solid was filtered off to give 12,500 g of perfluorinated compounds (I) (yield: 96%). The product was characterized as in Example 1.

I claim:

1. A process for the preparation of a perfluorinated ether of the formula (I)

$$R—CF_3—CF_3 \quad (I)$$

in which R is the radical $CF_3(CF_2)_2—O—[CF(CF_3)CF_2—O]_n—$, in which n is an integer from 0 to 60, from a compound of the formula (II)

$$R—[CF(CF_3)CF_2—O—]CHF—CF_3 \quad (II)$$

wherein R is defined above, which comprises heating the compound of the formula (II) at 150°-350° C. in the presence of at least one of the compounds $AlCl_3$, $AlBr_3$ or $AlF_3$.

2. The process as claimed in claim 1, wherein 1-100 mol % of at least one of the aluminum halides mentioned is used.

3. The process as claimed in claim 1, wherein 5-10 mol % of at least one of the aluminum halides mentioned is used.

4. The process as claimed in claim 1, wherein the reaction is carried out at 200°-280° C.

5. The process as claimed in claim 1, wherein the reaction is carried out at 240°-260° C.

* * * * *